US008378100B2

(12) United States Patent
Lynch et al.

(10) Patent No.: US 8,378,100 B2
(45) Date of Patent: Feb. 19, 2013

(54) PHOSPHONATE DERIVATIVES AS AUTOTAXIN INHIBITORS

(75) Inventors: Kevin R. Lynch, Charlottesville, VA (US); Timothy L. Macdonald, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 12/351,550

(22) Filed: Jan. 9, 2009

(65) Prior Publication Data

US 2010/0016258 A1 Jan. 21, 2010

Related U.S. Application Data

(60) Provisional application No. 61/019,949, filed on Jan. 9, 2008.

(51) Int. Cl.
*A61K 31/675* (2006.01)
*A61K 31/66* (2006.01)
*C07F 9/58* (2006.01)
*C07F 9/28* (2006.01)
*A61P 35/00* (2006.01)

(52) U.S. Cl. ............... 546/24; 564/15; 514/89; 514/120
(58) Field of Classification Search ........................ None
See application file for complete search history.

(56) References Cited

U.S. PATENT DOCUMENTS 6,852,316 B2 * 2/2005 Vinson et al. .............. 424/94.63
2006/0270634 A1 11/2006 Miller et al.

FOREIGN PATENT DOCUMENTS

WO   WO 2009/151644 A2   12/2009

OTHER PUBLICATIONS

Cui et al. in Bioorganic and Medicinal Chemistry Letters 17 (2007) 1634-1640.*
Cui et al. in Bioorganic and Medicinal Chemistry 16 (2008) 2212-2225.*
Heasley et al. in Bioorganic & Medicinal Chemistry Letter 14 (2004) 4069-4074.*
CAS STN Accession No. 2008:24647, entered Apr. 24, 2008. Cui, Peng, Ph.D. Dissertation No. 10B, p. 6664. Order No. AAI3286597. 242 pages. ISBN: 978-0-549-28936-4.*
Adams, P. et al., Biochem. J. 1974, vol. 141, pp. 729-732.
Aoki, J. et al. J. Biol. Chem. 2002, vol. 277, No. 50, pp. 48737-48744.
Baker, D.L. et al., J. Biol. Chem. 2006, vol. 281, No. 32, pp. 22786-22793.
Bollen, M. et al., Crit. Rev. Biochem. Mol. Biol. 2000, vol. 35, pp. 393-432.
Chakravarty, P. et al., Tetrahedron Lett. 1987, vol. 28, No. 6, pp. 611-612.
Contos, J. et al., J. Mol. Pharm. 2000, vol. 58, No. 6, pp. 1188-1196.
Cui, P. et al., Bioorg. Med. Chem. Lett. 2007, vol. 17, pp. 1634-1640.
Cui, P. et al., Bioorg. Med. Chem. 2008, vol. 16, pp. 2212-2225.

Deng, W. et al., Gastroenterology. 2002, vol. 123, pp. 206-216.
Dufour, M. et al., J. Chem. Soc. Perkin Trans. 1986, 1, pp. 1895-1899.
Durgam, G. G. et al., J. Med. Chem. 2005, vol. 48, pp. 4919-4930.
Durgam G. G. et al., Bioorg. Med. Chem. Lett. 2006, vol. 16, pp. 633-640.
Endo T, et al., J Biochem., 2009, vol. 146, pp. 283-293.
Ferry, G. et al., J. Biol Chem., 2003, vol. 278, No. 20, pp. 18162-18169.
Ferry, G. et al ., J Pharmacol Exp Ther. Dec. 2008;327(3):809-19.
Fuss, B. et al., J. Neurosci., 1997, vol. 17, No. 23, pp. 9095-9103.
Futagawa, S. et al., Bull. Chem. Soc. Jpn. 1973, vol. 46, pp. 3308-3310.
Gajewiak J. et al., Org Lett. 2008, vol. 10, 1111-1114.
Goding, J.W. et al., Immunol. Rev. 1998, vol. 161, pp. 11-26.
Goding J., J. Leukoc. Biol. 2000, vol. 67, pp. 285-311.
Gududuru V. et al., Bioorg. Med. Chem. Lett. 2006, vol. 16, pp. 451-456.
Heasley, B. H. et al., Bioorg. Med. Chem. Lett. 2004, vol. 14, pp. 2735-2740.
Heasley, B. H. et al., Bioorg. Med. Chem. Lett. 2004, vol. 14, pp. 4069-4074.
Hoeglund A.B. et al., Bioorg Med Chem. 2010, vol. 18, pp. 769-776.
Hoeglund A.B. et al., J Med Chem. 2010, vol. 53, 1056-1066.
Inoue M, et al., Mol Pain. 2008, vol. 4, pp. (online: http://www.molecularpain.com/content/pdf/1744-8069-4-6.pdf).
Karplus, M., J. Am. Chem. Soc. 1963, vol. 85, pp. 2870-2871.
Kawagoe, H. et al., Genomics. 1995, vol. 30, pp. 380-384.
Kehlen, A. et al., Int. J. Cancer. 2004, vol. 109, pp. 833-838.
Kishi, Y. et al., J. Biol. Chem. 2006, vol. 281, No. 25, pp. 17492-17500.
Lee, C. et al., J. Biol. Chem. 2006. vol. 281, No. 33, pp. 23589-23597.
Lee, C. et al., J. Biol. Chem. 2007, vol. 282, No. 7, pp. 4310-4317.
Lee, H. et al., Biochem. Biophys. Res. Commun. 1996, vol. 218, pp. 714-719.
Liu S, et al., Cancer Cell. 2009, vol. 15, 539-550.
Lynch, K. R. et al., Prost. Lipid Med. 2001, vol. 64, pp. 33-45.
McIntyre, T. et al., Proc. Natl. Acad. Sci., 2003, vol. 100, No. 1, pp. 131-136.
Mills, G. B. et al., Nat. Rev., Cancer. 2003, vol. 3, pp. 582-591.
Nam, S.W. et al., Oncogene., 2000, vol. 19, pp. 241-247.
Nam, S.W. et al., Cancer Res. ,2001, vol. 61, pp. 6938-6944.
Narita, M. et al., J. Biol. Chem. ,1994, vol. 269, No. 45, pp. 28235-28242.
Nieschalk, J. et al., Tetrahedron,1996, vol. 52, No. 1, pp. 165-176.
Noguchi, K. et al., J. Biol. Chem., 2003, vol. 278, No. 28, pp. 25600-25606.
North E.J. et al., Bioorg. Med. Chem., 2009, vol. 17, pp. 3433-3442.
Qian, L. et al., Chem. Med. Chem., 2006, vol. 1, pp. 376-383.
Rabinowitz, R. J. Org. Chem., 1963, vol. 28, p. 2975-2978.
Saunders L. et al., Mol Cancer Ther., 2008, vol. 7,3352-3362.
Sano, T. et al., J. Biol. Chem., 2002, vol. 277, No. 24, pp. 21197-21206.
Santos, W. et al., Bioorg. & Med. Chem. Lett., 2004, vol. 14, pp. 3473-3476.
Siess, W. et al., Proc. Natl. Acad. Sci., 1999, vol. 96, pp. 6931-6936.

(Continued)

*Primary Examiner* — Dennis Heyer
(74) *Attorney, Agent, or Firm* — Rodney L. Sparks

(57) ABSTRACT

The present invention provides β-hydroxy phosphonate compounds that are autotaxin inhibitors.

12 Claims, 3 Drawing Sheets

OTHER PUBLICATIONS

Song, J. et al., Biochem. Biophys. Res. Commun., 2005, vol. 337, pp. 967-975.
Stefan, C. et al., Biochem. Biophys. Acta., 1999, vol. 1450, pp. 45-52.
Stracke, M. et al., J. Biol. Chem., 1992, vol. 267, No. 4, pp. 2524-2529.
Stracke, M.L. et al., Adv. Enzyme Regul., 1997, vol. 37, pp. 135-144.
Sturm, A. et al., Gastroenterology., 1999, vol. 117, pp. 368-377.
Sturm, A. et al., Biochim. Biophys. Acta., 2002, vol. 1582, pp. 282-288.
Sugiura, T. et al., J. Lipid Res. 2002, vol. 43, pp. 2049-2055.
Tamaruya, Y. et al., Angew. Chem. Int. Ed. 2004, vol. 43, pp. 2834-2837.
Tigyi, G. et al., Prog. Lipid Res. 2003, vol. 42, pp. 498-526.
Tokumura, A. et al., J. Biol. Chem. 2002, vol. 277, No. 42, pp. 39436-39442.
Uchiyama, A. et al., Biochem. Biophys. Acta 2007, vol. 1771, pp. 103-112.
Umezu-Goto, M. et al., J. Cell Biol. 2002, vol. 158, No. 2, pp. 227-233.
Umezu-Goto, M. et al., J. Cell Biochem. 2004, vol. 92, pp. 1115-1140.
van Meeteren L.A. et al., J. Biol. Chem., 2005, vol. 280, No. 22, pp. 21155-21161.
van Meeteren L.A. et al., Cancer Lett., Aug. 8, 2008;266(2), pp. 203-208.
Xu Y. et al., Biochem J. 1995, vol. 309, pp. 933-940.
Xu, Y. et al., Clin. Cancer Res. 1995, vol. 1, pp. 1223-1232.
Xu, Y. et al., J. Org. Chem., 2003, vol. 68, pp. 5320-5330.
Xu, Y. et al., Org. Lett. 2003, vol. 5, No. 13, pp. 2267-2270.
Xu X., et al., Prostaglandins Other Lipid Mediat., 2009, vol. 89, pp. 140-146.
Yang, S. et al., Clin. Exp. Metastasis., 2002, vol. 19, pp. 603-608.
Zhang, C. et al., J. Exp. Med., 2004, vol. 199, No. 6, pp. 763-774.
Zhang, H et al., Cancer Res., 2009; 69, pp. 5441-5449.

\* cited by examiner

Scheme 1

Reagents and conditions: (i) acyl chloride, Et$_3$N, CH$_2$Cl$_2$, 0°C, 3hr, 70-80%; (ii) mesylate, K$_2$CO$_3$, 18-crown-6, acetone, reflux overnight, 90-95%; (iii) n-BuLi, dimethyl methylphosphonate, then add in ester c, -78°C, 3hr, 50-60%; (iv) NaBH$_4$, THF, EtOH, 0°C, 2hr, 70-80%; (v) bromotrimethylsaline, w/wo pyridine, CH$_2$Cl$_2$, rt, 4hr, then H$_2$O and MeOH, 90-95%.

PHOSPHONATE DERIVATIVES AS AUTOTAXIN INHIBITORS

CROSS-REFERENCE TO RELATED APPLICATION

This application claims priority from U.S. Provisional Application Ser. No. 61/019,949, filed Jan. 9, 2008.

US GOVERNMENT RIGHTS

This invention was made with United States Government support under Grant No. R01 GM052722 awarded by the National Institute of Health. The United States Government has certain rights in this invention.

BACKGROUND OF THE INVENTION

Autotaxin (ATX) is an autocrine motility factor that promotes cancer cell invasion, cell migration and angiogenesis. ATX, originally discovered as a nucleotide phosphodiesterase, is known now to be responsible for the lysophospholipid-preferring phospholipase D activity in plasma. As such, it catalyzes the production of lysophosphatidic acid (LPA) from lysophosphatidylcholine (LPC). ATX is thus an attractive drug target; small molecular inhibitors might be efficacious in slowing the spread of cancers. With this study we have generated a series of beta-keto and beta-hydroxy phosphonate derivatives of LPA, some of which are potent ATX inhibitors.

The autocrine motility factor autotaxin (ATX) was originally isolated from melanoma cell supernatants as a 125-kD glycoprotein that stimulated tumor cell motility. In vivo experiments documented that forced expression of ATX augments tumor cell invasion and metastasis. Further, ATX promotes angiogenesis and may act in concert with other angiogenic factors to facilitate new blood vessel formation. These biological properties require enzymatic activity.

ATX belongs to the nucleotide pyrophosphatase and phosphodiesterase (NPP) family of enzymes, which hydrolyze phosphodiester and diphosphate bonds, typically found in ATP and ADP. Interest in ATX was stimulated by the identification of this enzyme as the long elusive plasma lysophospholipase D activity, which is responsible for the cleavage of choline group of lysophosphatidylcholine (LPC) to form lysophosphatidic acid (LPA). This is a major pathway of biosynthesis of LPA in plasma. LPA is an intercellular lipid mediator that influences many biochemical processes including cell proliferation, smooth muscle contraction, platelet aggregation and apoptosis. For example, LPA is the "ovarian cancer activating factor" in ascitic fluid characteristic of ovarian cancer patients. Elevated levels of LPA are present both at early and late stages in ovarian cancer and may play a role in tumor cell proliferation and invasion. LPA mediates its effects through the activation of G protein-coupled receptors (GPCR). Thus, great efforts have been made on the study of LPA receptor antagonists and agonists due to their therapeutic potential. In aggregate, these data suggest that ATX is an attractive pharmacological target; blockage of LPA production via ATX inhibition by small molecules could be a useful anticancer chemotherapy. A limited number of ATX inhibitors that are LPA analogs are known.

Currently, there is a need for novel, potent, and selective compounds that inhibit ATX. These compounds can be useful for preventing or treating cancer. The present invention satisfies these needs.

SUMMARY

The present invention provides in one aspect compounds that can inhibit ATX receptors. The compounds are phosphonate analogs that can inhibit the receptors. Accordingly, there is provided a compound of formula IA or IB:

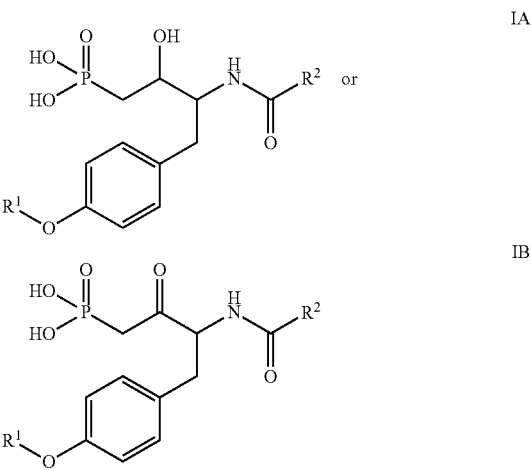

wherein $R^1$ is $C_1$-$C_6$ alkyl, or methyl substituted with cyclohexyl, phenyl, pyridyl; where the cyclohexyl, phenyl, or pyridyl are optionally substituted with methyl, methoxy, or 2,2,2-trifluoroethyoxy; $R^2$ is $C_9$-$C_{19}$ alkyl; or a pharmaceutically acceptable salt or isomer thereof.

The present invention also provides pro-drugs of any of the compounds of formula IA or IB to increase oral availability.

In another aspect, the present invention also provides:

a method for inhibiting angiogenesis in a tumor, including contacting the cancerous cells with an effective amount of a compound of formula IA or IB, a pharmaceutically acceptable salt or ester thereof;

a compound of formula IA or IB, or a pharmaceutically acceptable salt thereof for use in medical treatment (for example, treatment of neoplastic disease, prevention of angiogenesis or cell migration).

In another aspect, the invention provides the use of a compound of formula IA or IB, a pharmaceutically acceptable salt or ester thereof to prepare a medicament for inhibiting tumor growth, treatment of neoplastic disease, metastasis or tumor angiogenesis or cell migration in a mammalian species (for example, a human).

In another aspect, the invention provides the use of a compound of formula IA or IB, a pharmaceutically acceptable salt or ester thereof to prepare a medicament for inhibiting fibrosis, treatment of fibrotic diseases, most specifically pulmonary fibrosis and/or renal fibrosis.

In another aspect, the invention provides the use of a compound of formula IA or IB, a pharmaceutically acceptable salt or ester thereof to prepare a medicament for treating chronic pain syndromes, specifically neuropathic pain resulting from trauma, diabetes or viral infections.

In another aspect, the invention provides a compound of formula IA or IB, a pharmaceutically acceptable salt or ester thereof for use in medical treatment (for example, treatment of neoplastic disease).

In another aspect, the present invention provides compositions and methods for the use of the disclosed compounds to inhibit ATX and ATX inhibiting pro-drugs for the treatment of neoplastic diseases. In one aspect, this treatment is effected by administration of ATX inhibitors that are efficacious by virtue of their anti-angiogenic properties.

In another aspect, the invention provides novel intermediates and processes disclosed herein that are useful for preparing compounds of formula IA or IB, including the generic and specific intermediates as well as the synthetic processes described herein.

In another aspect, the present invention provides synthetic schemes and methods of use of compounds having formula IA or IB and analogs or derivatives thereof. In another aspect, the invention provides synthetic and modification schemes for preparing analogs and derivatives of the compounds of formula IA or IB, as well as compositions and methods for the use of such analogs and derivatives.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

The invention also provides a pharmaceutical composition comprising a compound of formula IA or IB, in combination with LPA receptor antagonist or pharmaceutically acceptable salts thereof, in combination with a pharmaceutically acceptable diluent or carrier.

The invention also provides a pharmaceutical composition comprising a compound of formula IA or IB, or a pharmaceutically acceptable salt thereof, in combination with a pharmaceutically acceptable diluent or carrier.

The details of one or more embodiments of the invention are set forth in the accompanying description below. Other features, objects, and advantages of the invention will be apparent from the description and drawings, and from the claims.

BRIEF DESCRIPTION OF THE DRAWINGS

In FIG. 3, the results were fitted to a straight line by linear regression. The apparent Km for LPC was about 588 µM.

DETAILED DESCRIPTION

Figure 1:
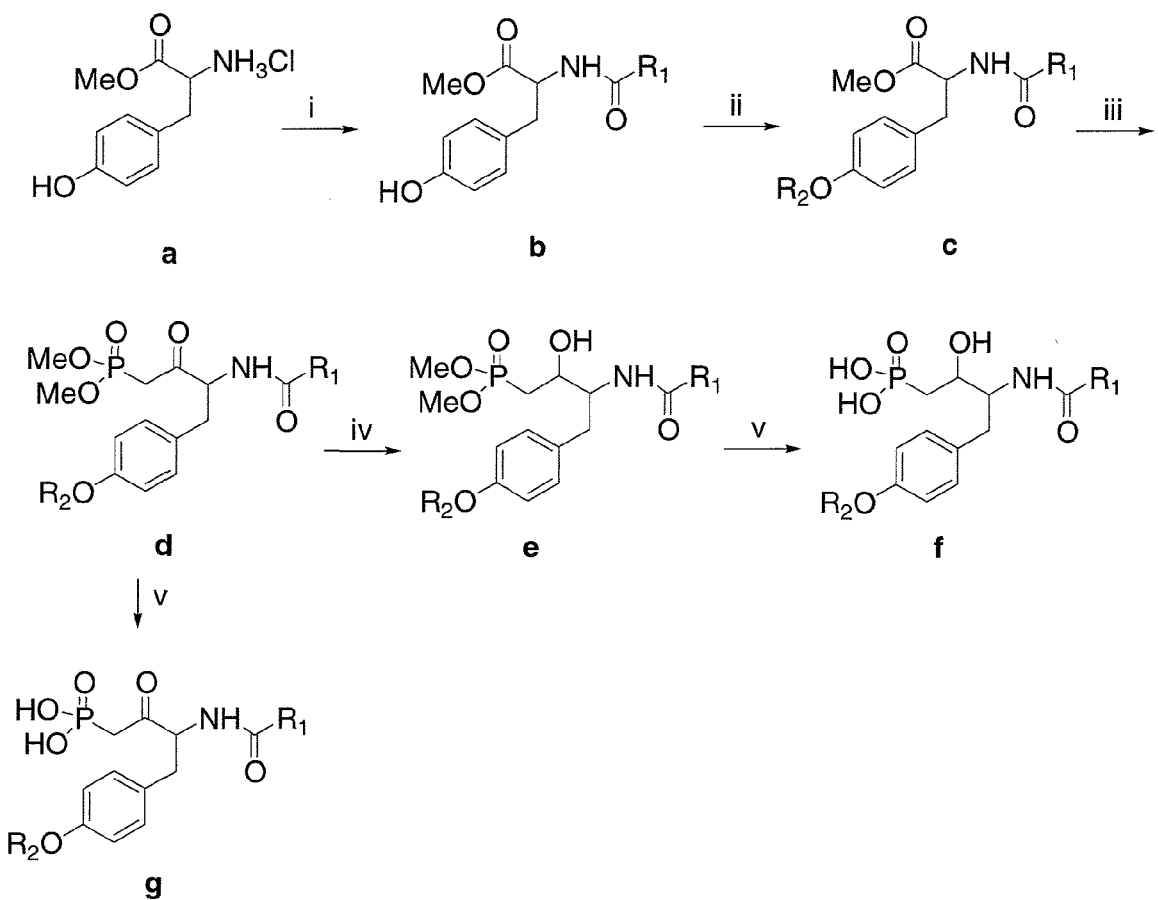
FIG. 1 illustrates a general synthesis of the disclosed compounds.

In describing and claiming the invention, unless otherwise defined, all technical and scientific terms used herein have the same meaning as commonly understood by one of ordinary skill in the art to which this invention belongs. Although any materials and methods similar or equivalent to those described herein can be used in the practice or testing of the present invention, the preferred materials and methods are described herein. Each of the following terms has meaning associated with it in this section. Specific and preferred values listed below for radicals, substituents, and ranges are for illustrations only; they do not exclude other defined values or other values within defined ranges for the radicals and substituents.

The terms "a," "an," "the," "at least one," and "one or more" are used interchangeably. Thus, for example, a composition that comprises "an" element means one element or more than one element.

The term "affected cell" refers to a cell of a subject afflicted with a disease or disorder, which affected cell has an altered phenotype relative to a subject not afflicted with a disease or disorder.

Cells or tissue are "affected" by a disease or disorder if the cells or tissue have an altered phenotype relative to the same cells or tissue in a subject not afflicted with a disease or disorder.

A disease or disorder is "alleviated" if the severity of a symptom of the disease or disorder, the frequency with which such a symptom is experienced by a patient, or both, is reduced.

An "analog" of a chemical compound is a compound that, by way of example, resembles another in structure but is not necessarily an isomer (e.g., 5-fluorouracil is an analog of thymine).

The terms "cell," "cell line," and "cell culture" may be used interchangeably.

A "control" cell, tissue, sample, or subject is a cell, tissue, sample, or subject of the same type as a test cell, tissue, sample, or subject. The control may, for example, be examined at precisely or nearly the same time the test cell, tissue, sample, or subject is examined. The control may also, for example, be examined at a time distant from the time at which the test cell, tissue, sample, or subject is examined, and the results of the examination of the control may be recorded so that the recorded results may be compared with results obtained by examination of a test cell, tissue, sample, or subject. The control may also be obtained from another source or similar source other than the test group or a test subject, where the test sample is obtained from a subject suspected of having a disease or disorder for which the test is being performed.

A "test" cell, tissue, sample, or subject is one being examined or treated.

A "pathoindicative" cell, tissue, or sample is one which, when present, is an indication that the animal in which the cell, tissue, or sample is located (or from which the tissue was obtained) is afflicted with a disease or disorder. By way of example, the presence of one or more breast cells in a lung tissue of an animal is an indication that the animal is afflicted with metastatic breast cancer.

A tissue "normally comprises" a cell if one or more of the cell are present in the tissue in an animal not afflicted with a disease or disorder.

A "disease" is a state of health of an animal wherein the animal cannot maintain homeostasis, and wherein if the disease is not ameliorated then the animal's health continues to deteriorate.

A "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" means an amount sufficient to produce a selected effect. For example, an effective amount of an LPA receptor antagonist is an amount that decreases the cell signaling activity of the LPA receptor.

A "functional" molecule is a molecule in a form in which it exhibits a property by which it is characterized. By way of example, a functional enzyme is one which exhibits the characteristic catalytic activity by which the enzyme is characterized.

The term "inhibit" refers to the ability of a disclosed compound to reduce or impede a described function. Preferably, inhibition is by at least 10%, more preferably by at least 25%, even more preferably by at least 50%, and most preferably, the function is inhibited by at least 75%.

"Instructional material" includes a publication, a recording, a diagram, or any other medium of expression which can be used to communicate the usefulness of the disclosed compounds in the kit for effecting alleviation of the various diseases or disorders recited herein. Optionally, or alternately, the instructional material may describe one or more methods of alleviating the diseases or disorders in a cell or a tissue of a mammal. The instructional material of the kit may, for example, be affixed to a container which contains a disclosed compound or be shipped together with a container which contains the identified compound. Alternatively, the instructional material may be shipped separately from the container with the intention that the instructional material and the compound be used cooperatively by the recipient.

The term "parenteral" means not through the alimentary canal but by some other route such as subcutaneous, intramuscular, intraspinal, or intravenous.

The term "purified" and similar terms relate to the isolation of a molecule or compound in a form that is substantially free (at least 75% free, preferably 90% free, and most preferably at least 95% free) from other components normally associated with the molecule or compound in a native environment. The term "purified" does not necessarily indicate that complete purity of the particular molecules achieved during the process. A "very pure" compound refers to a compound that is greater than 90% pure. A "highly purified" compound refers to a compound that is greater than 95% pure.

A "sample" refers preferably to a biological sample from a subject, including, but not limited to, normal tissue samples, diseased tissue samples, biopsies, blood, saliva, feces, semen, tears, and urine. A sample can also be any other source of material obtained from a subject, which contains cells, tissues, or fluid of interest. A sample can also be obtained from cell or tissue culture.

The term "standard," refers to something used for comparison. For example, a standard can be a known standard agent or compound which is administered or added to a control sample and used for comparing results when measuring said compound in a test sample. Standard can also refer to an "internal standard," such as an agent or compound that is added at known amounts to a sample and is useful in determining such things as purification or recovery rates when a sample is processed or subjected to purification or extraction procedures before a marker of interest is measured.

A "subject" of analysis, diagnosis, or treatment is an animal. Such animals include mammals, preferably a human.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

The term "treating" includes prophylaxis of the specific disorder or condition, or alleviation of the symptoms associated with a specific disorder or condition or preventing or eliminating said symptoms.

The disclosed compounds are generally named according to the IUPAC or CAS nomenclature system. Abbreviations which are well known to one of ordinary skill in the art may be used (e.g., "Ph" for phenyl, "Me" for methyl, "Et" for ethyl, "h" for hour or hours, "rt" for room temperature, and "rac" for racemic mixture).

The values listed below for radicals, substituents, and ranges, are for illustration only; they do not exclude other defined values or other values within defined ranges for the radicals and substituents. The disclosed compounds include compounds of formula IA or IB having any combination of the values, specific values, more specific values, and preferred values described herein.

The term "$C_1$-$C_{19}$ alkyl" refers to a branched or linear alkyl group having from one to nineteen carbon atoms. Non-limiting examples include, but are not limited to, methyl, ethyl, n-propyl, iso-propyl, butyl, iso-butyl, sec-butyl, tert-butyl, pentyl, hexyl, heptyl, octyl and the like.

The term "optionally substituted" refers to zero, one, two, three or four substituents, wherein the substituents are each independently selected. Each of the independently selected substituents may be the same or different than other substituents.

The term "phosphate analog", "phosphate ester", "phosphonate ester" and "phosphonate analog" comprise analogs of phosphate and phosphonate wherein the phosphorous atom is in the +5 oxidation state and one or more of the oxygen atoms is replaced with a non-oxygen moiety, including for example, the phosphate analogs phosphorothioate, phosphorodithioate, phosphoroselenoate, phosphorodiselenoate, phosphoroanilothioate, phosphoranilidate, phosphoramidate, boronophosphates, and the like, including associated counterions, e.g., H, $NH_4$, Na, K, and the like if such counterions are present.

A "derivative" of a compound refers to a chemical compound that may be produced from another compound of similar structure in one or more steps, such as replacement of hydrogen by an alkyl, acyl, or amino group.

The term "pharmaceutically acceptable carrier" includes any of the standard pharmaceutical carriers, such as a phosphate buffered saline solution, hydroxypropyl beta-cyclodextrins (HO-propyl beta cyclodextrins), water, emulsions such as an oil/water or water/oil emulsion, and various types of wetting agents. The term also encompasses any of the agents approved by a regulatory agency of the US Federal government or listed in the US Pharmacopeia for use in animals, including humans.

The term "pharmaceutically-acceptable salt" refers to salts that retain the biological effectiveness and properties of the disclosed compounds and that are not biologically or otherwise undesirable. In many cases, the disclosed compounds are capable of forming acid or base salts by virtue of the presence of amino or carboxyl groups or groups similar thereto.

An "effective amount" means an amount sufficient to produce a selected effect. For example, an effective amount of an ATX inhibitor is an amount that decreases the cell activity of the ATX enzyme.

The disclosed compounds can contain one or more asymmetric centers in the molecule. In accordance with the present disclosure any structure that does not designate the stereochemistry is to be understood as embracing all the various optical isomers, as well as racemic mixtures thereof.

It will be appreciated by those skilled in the art that the disclosed compounds having chiral centers may exist in and be isolated in optically active and racemic forms. It is to be understood that the disclosed compounds encompass any racemic, optically active or stereoisomeric form, or mixtures thereof, of the compound, which possess the useful properties described herein, such as the S,R; S,S; R,R; or R,S diastereomers. It is well known in the art how to prepare such optically active forms (for example, by resolution of the racemic form by recrystallization techniques, by synthesis from optically-active starting materials, by chiral synthesis, or by chromatographic separation using a chiral stationary phase) and how to determine LPA agonist activity using the standard tests described herein, or using other similar tests which are well known in the art. In addition, some compounds may exhibit polymorphism.

The present invention is also includes pharmaceutical compositions including the compounds of the present invention. More particularly, such compounds can be formulated as pharmaceutical compositions using standard pharmaceutically acceptable carriers, fillers, solubilizing agents and stabilizers known to those skilled in the art. For example, a pharmaceutical composition having a compound of the invention, or analog, derivative, or modification thereof, as described herein, is used to administer the appropriate compound to a subject.

The compounds of the invention are useful for treating a disease or disorder including administering to a subject in need thereof of a therapeutically acceptable amount of a compound of formula IA or IB, or a pharmaceutical composition including a therapeutically effective amount of a compound of formula IA or IB, and a pharmaceutically-acceptable carrier.

An exemplary synthesis for preparing the disclosed compounds, e.g., compounds f and g. is provided in Scheme 1. The synthesis begins with the acylation of the ammonium hydrochloride salt of tyrosine O-methyl ester, a, with a suitable acyl chloride followed by etherification of the free phenol with appropriate mesylates to afford the fully protected tyrosine, c. Next, is the base mediated addition onto the methyl ester with the lithium anion of dimethyl methylphosphonate to achieve β-keto phosphonate dimethyl ester, d. A bromotrimethylsaline mediated deprotection of the ester ensues to afford the β-keto phosphonate, g. Sodium borohydride reduction of, d, proceeds to furnish two possible diastereometic β-hydroxy phosphonate dimethyl esters which can be separated by column chromatography. The β-hydroxy phosphonate, f, is obtained by using the same deprotection method (for compounds f41 and f42, pyridine was used in the deprotection).

Specific and preferred values listed below for radicals, substituents, and ranges, are for illustration only; they do not exclude other defined values or other values within defined ranges for the radicals and substituents.

Exemplary values for $R^1$ are $CH_3$, $n\text{-}C_3H_7$, $n\text{-}C_5H_{11}$, $i\text{-}C_5H_{11}$,

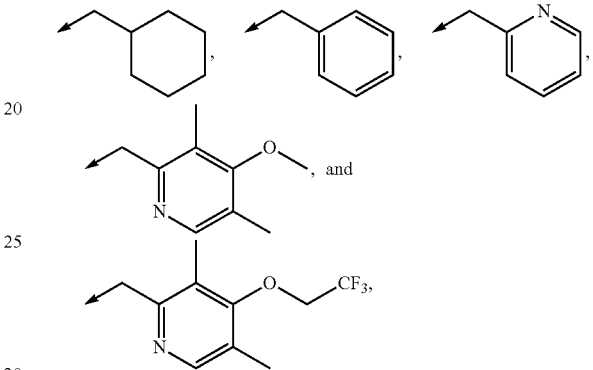

where the arrow indicates the location of the bond which links the $R^1$ group to the oxygen atom in the core.

Exemplary values for $R^2$ are $n\text{-}C_9H_{19}$, $n\text{-}C_{13}H_{27}$, $n\text{-}C_{15}H_{31}$, $n\text{-}C_{17}H_{33}$, $n\text{-}C_{17}H_{35}$, and $n\text{-}C_{19}H_{39}$, wherein the $n\text{-}C_{17}H_{33}$ group has a cis double bond located between C9 and C10, counted from the carbonyl carbon atom.

Specific compounds of the invention have the general formulas IIA, IIB, and IIC are illustrated in Tables 1, 2, and 3.

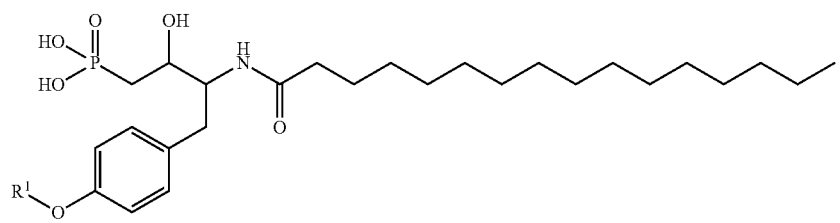

IIA

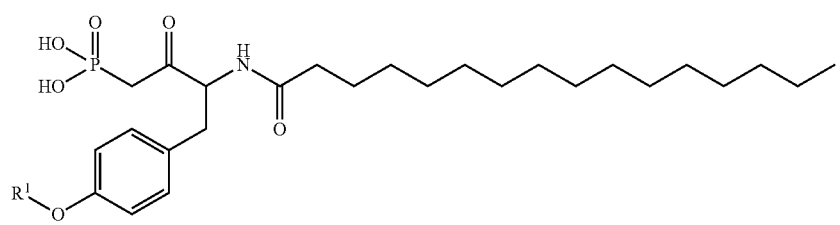

IIB

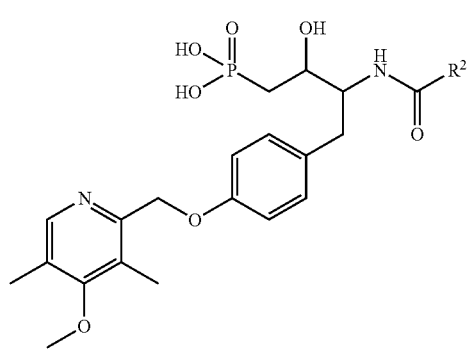

IIC

Additional compounds have the formulas

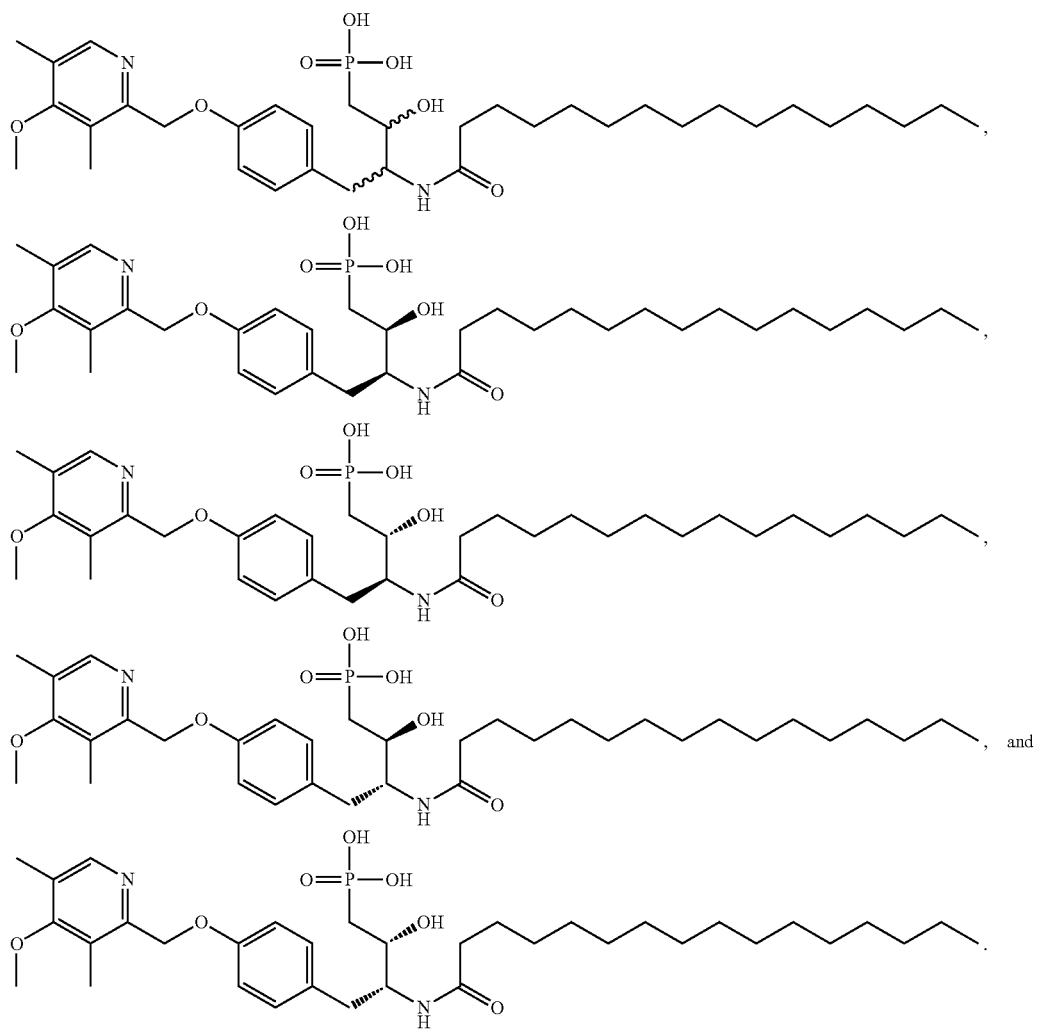

, and

In cases where compounds of formula IA or IB are sufficiently basic or acidic to form stable nontoxic acid or base salts, preparation and administration of the compounds as pharmaceutically acceptable salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion.

Alkali metal (for example, sodium, potassium or lithium) or alkaline earth metal (for example calcium) salts of carboxylic acids can also be made.

Pharmaceutically acceptable base addition salts can be prepared from inorganic and organic bases. Salts from inorganic bases, include but are not limited to, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl)amines, tri(substituted alkyl) amines, alkenyl amines, dialkenyl amines, trialkenyl amines, substituted alkenyl amines, di(substituted alkenyl)amines, tri(substituted alkenyl)amines, cycloalkyl amines, di(cycloalkyl)amines, tri(cycloalkyl)amines, substituted cycloalkyl amines, disubstituted cycloalkyl amine, trisubstituted cycloalkyl amines, cycloalkenyl amines, di(cycloalkenyl)amines, tri(cycloalkenyl)amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are alkyl, substituted alkyl, alkenyl, substituted alkenyl, cycloalkyl, substituted cycloalkyl, cycloalkenyl, substituted cycloalkenyl, aryl, heteroaryl, or heterocyclic and the like. Also included are amines where the two or three substituents, together with the amino nitrogen, form a heterocyclic or heteroaryl group. Non-limiting examples of amines include, isopropylamine, trimethyl amine, diethyl amine, tri(iso-propyl)amine, tri(n-propyl)amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful, for example, carboxylic acid amides, including carboxamides, lower alkyl carboxamides, dialkyl carboxamides, and the like.

The compounds of formula IA or IB can be formulated as pharmaceutical compositions and administered to a mammalian host, such as a human patient in a variety of forms adapted to the chosen route of administration, e.g., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least about 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Exemplary pharmaceutical dosage forms for injection or infusion can include sterile aqueous solutions or dispersions or sterile powders having the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium including, for example, water, ethanol, a polyol (for example, glycerol, propylene glycol, liquid polyethylene glycols, and the like), vegetable oils, nontoxic glyceryl esters, and mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, e.g., when they are liquids. However, it will generally be desirable to administer them to the skin as compositions or formulations, in combination with a dermatologically acceptable carrier, which may be a solid or a liquid.

Exemplary solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula IA or IB to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula IA or IB can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula IA or IB in a liquid composition, such as a lotion, will be from about 0.1 to about 25 weight percent, preferably from about 0.5-10 weight percent. The concentration in a semi-solid or solid composition such as a gel or a powder will be about 0.1-5 weight percent preferably about 0.5-2.5 weight percent based on the total weight of the composition.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 µM, preferably, about 1 to 50 µM, most preferably, about 2 to about 30 µM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four, or more sub-doses per day. The sub-dose itself may be further divided, e.g., into a number of discrete loosely spaced administrations; such as multiple inhalations from an insufflator or by application of a plurality of drops into the eye.

The disclosed method includes a kit including an inhibitor compound of formula IA or IB and instructional material that describes administering the inhibitor compound or a composition including the inhibitor compound to a cell or a subject. This should be construed to include other embodiments of kits that are known to those skilled in the art, such as a kit having a (preferably sterile) solvent for dissolving or suspending the inhibitor compound or composition prior to administering the compound or composition to a cell or a subject. Preferably, the subject is a human.

The disclosed compounds and methods, as described above or as discussed in the Examples below, there can be employed conventional chemical, cellular, histochemical, biochemical, molecular biology, microbiology, and in vivo techniques which are known to those of skill in the art. Such techniques are explained fully in the literature.

Without further description, it is believed that one of ordinary skill in the art can, using the preceding description and the following illustrative examples, make and utilize the disclosed compounds.

Processes for preparing compounds of formula IA or IB or for preparing intermediates useful for preparing compounds of formula IA or IB are provided as further embodiments. Intermediates useful for preparing compounds of formula IA or IB are also provided as further embodiments. The processes are provided as further embodiments and are illustrated in the schemes herein wherein the meanings of the generic radicals are as given above unless otherwise qualified. A general method for preparing the disclosed compounds is illustrated in Scheme 1, FIG. 1.

The invention is now described with reference to the following Examples and Embodiments. Without further description, it is believed that one of ordinary skill in the art can, using the preceding description and the following illustrative examples, make and utilize the disclosed compounds. The following working examples therefore, are provided for the purpose of illustration only and specifically point out the preferred embodiments, and are not to be construed as limiting in any way the remainder of the disclosure. Therefore, the examples should be construed to encompass any and all variations which become evident as a result of the teaching provided herein.

All non-aqueous reactions were carried out in oven or flame-dried glassware under an argon or nitrogen atmosphere with dry solvents and magnetic stirring, unless otherwise stated. The argon and nitrogen were dried by passing through a tube of Drierite. Anhydrous diethyl ether ($Et_2O$), toluene, dichloromethane ($CH_2Cl_2$), methanol (MeOH), and tetrahydrofuran (THF) were purchased from Aldrich or VMR Chemicals and used as received. All other reagents were purchased from Acros chemicals and Aldrich chemicals. Except as indicated otherwise, reactions were monitored by thin layer chromatography (TLC) using 0.25 mm Whatman precoated silica gel plates. Flash chromatography was performed with the indicated solvents and Dynamic Adsorbents silica gel (particle size 0.023-0.040 mm). Radial chromatography performed with a Chromatotron from Harrison Research Laboratories utilizing pre-coated rotors from Analtech.

Proton ($^1H$) and carbon ($^{13}C$) NMR spectra were recorded on a Varian UnityInova 500/51 or Varian UnityInova 300/54 at 300K unless otherwise noted. Chemical shifts are reported in ppm (δ) values relative to the solvent as follows: $CDCl_3$ (δ 7.24 for proton and δ 77.0 for carbon NMR) and DMSO-$d_6$ (δ 2.50 for proton and δ 39.5 for carbon NMR).

Other abbreviations: acetonitrile (MeCN), acetic acid (AcOH), chloroform ($CHCl_3$), ethyl acetate (EtOAc), isopropanol (i-PrOH), methanol (MeOH), trifluoroacetic acid (TFA), water ($H_2O$), hydrochloric acid (HCl), sodium sulfate ($Na_2SO_4$), sodium bicarbonate ($NaHCO_3$), potassium carbonate ($K_2CO_3$), phosphorus pentoxide ($P_2O_5$), lithium hydroxide (LiOH), aqueous (aq.), hour (h), minute (min), room temperature (r.t.).

EXAMPLE 1

Synthesis of Compound f17

(R)-3-(4-hydroxyphenyl)-2-palmitamidopropanoic acid

To a solution of L-Tyrosine methyl ester hydrochloride (1 g, 4.3 mmol) in $CH_2Cl_2$ was added triethylamine (1.49 mL, 8.6 mmol) at room temperature. Palmitoyl chloride (1.53 g, 5.6 mmol) was then added to the reaction mixture at 0° C. After the reaction was completed, as judged by TLC, the reaction mixture was quenched and extracted with 1 N HCl (3×5 mL) then saturated sodium bicarbonate (1×5 mL). The combined organic layers were dried with $Na_2SO_4$ and evaporated under vacuum to a white solid (1.86 g, 4.3 mmol). The product was carried on without further purification. $^1$H NMR (300 MHz, $CDCl_3$, 23° C., 6): 6.94 (d, 1H, J=8.5), 6.73 (d, 1H, J=8.5), 5.92 (d, 1, H, J=8.0), 4.90 (d, 1H, J=5.8), 4.85 (d, 1H, J=5.8), 3.73 (s, 3H), 3.04 (ddd, 1H, J=5.8, 14.0, 27.7), 2.26-2.12 (m, 1H), 1.58 (m, 2H), 1.25 (m, 24H), 0.90 (t, 3H, J=6.67).

(R)-3-(4-((4-methoxy-3,5-dimethylpyridin-2-yl)methoxy)phenyl)-2-palmitamidopropanoic acid To a solution of the phenol (1.86 g, 4.3 mmol) $K_2CO_3$ (2.97 g, 21.5 mmol) and 18-crown-6 (113 mg, 0.43 mmol) in acetone (25 mL) was added 4-methoxy-3,5-dimethyl-pyridin-2-ylmethanesulfonate (2.1 g, 8.6 mmol). The solution was then refluxed for 12 hours. The solvent was removed under reduced pressure and the resulting oil was extracted with water (3×5 mL). The organic layer was dried with $Na_2SO_4$, filtered, and evaporated under reduced pressure. The product was isolated using flash chromatography (1:1 EtOAc: Hexanes, $R_f$=0.26) to yield the product as an oil 1.62 g (62%). $^1$H NMR (300 MHz, $CDCl_3$, 23° C., 6): 8.22 (s, 1H), 6.95 (q, 5H, J=8.8), 5.91 (d, 1H, J=7.8), 5.11 (s, 2H), 4.84 (dd, 1H, J=5.7, 13.5), 3.76 (s, 3H), 3.70 (s, 3H), 3.12-2.95 (m, 2H), 2.31 (s, 3H), 2.20 (s, 3H), 2.19-2.09 (m, 2H), 1.57 (m, 2H), 1.23 (m, 24H), 0.86 (t, 3H, J=6.7). $^{13}$C NMR (300 MHz, $CDCl_3$, 23° C., 6) 10.89, 13.29, 14.04, 22.64, 25.50, 29.18, 29.29, 29.45, 29.65, 31.88, 36.54, 37.03, 52.18, 52.95, 70.85, 114.94, 126.35, 128.11, 130.19, 149.00, 157.92, 164.33, 172.21, 172.58.

(S)-methyl 3-(4-((4-methoxy-3,5-dimethylpyridin-2-yl)methoxy)phenyl)-2-palmitamidopropanoate To a solution of dimethyl methyl phosphonate (885 uL, 8.28 mmol, 4.00 eq) in THF (30 mL) at −78° C. was added nBuLi (3.45 mL, 8.28 mmol, 4.00 eq) by syringe over 10 min. After letting the reaction stir for an additional 10 min, the methyl ester was added at −78° C. in THF (10 mL) by syringe over 10 min. The reaction was stirred for 2 h at −78° C. and subsequently quenched with 1N HCl (1 mL), then neutralized with 10% $NaHCO_3$ 100 mL and extracted with three portions of ethyl acetate (3×100 mL). The organic layers were collected, dried with sodium sulfate, and concentrated under reduced pressure. The mixture was purified via flash chromatography (silica gel, 5% MeOH in $CHCl_3$) to yield 1.11 g (1.91 mmol, 92%) of (S)-methyl 3-(4-((4-methoxy-3,5-dimethylpyridin-2-yl)methoxy)phenyl)-2-palmitamidopropanoate as a clear and colorless oil: $R_f$=0.42 (5% MeOH in $CHCl_3$); $^1$H NMR (500 MHz, $CDCl_3$ δ 8.17 (s, 1H), 7.03 (d, 2H, J=8.5), 6.88 (d, 2H, J=8.5), 6.58 (d, 1H, J=7.8), 5.06 (s, 2H), 4.79 (dd, 1H, J=7.5, 13.6), 3.70 (m, 9H), 3.19 (dd, 1H, J=14.1, 22.3), 3.05 (m, 2H), 2.88 (dd, 1H, J=7.5, 14.3), 2.26 (s, 3H), 2.21 (s, 3H), 2.12 (td, 2H, J=1.4, 7.1), 1.50 (m, 2H), 1.42 (dd, 1H, J=0.5, 17.5), 1.19 (m, 24H), 0.82 (t, 1H, J=6.9); $^{13}$C NMR (75 MHz, $CDCl_3$) δ 200.74, 173.09, 164.26, 157.72, 154.12, 148.97, 130.21, 128.58, 126.36, 114.88, 70.74, 59.86, 59.82, 53.19, 52.99, 52.18, 39.27, 38.24, 36.32, 35.52, 31.86, 29.63, 29.43, 29.29, 29.19, 25.46, 22.63, 14.07, 13.31, 10.87.

(S)-dimethyl 2-hydroxy-4-(4-((4-methoxy-3,5-dimethylpyridin-2-yl)methoxy)phenyl)-3-palmitamidobutylphosphonate In a dry round bottom flask charged with nitrogen and 1 mL of a 1:1 solution of anhydrous ethanol and anhydrous tetrahydrofuran at room temperature was added the α-ketophosphonate (0.105 g, 1 eq.) followed by of cerium chloride hepta hydrate (0.075 g, 1.3 eq.). To a second dry round bottom flask was added 0.5 mLs of anhydrous ethanol followed by sodium borohydride (0.4 g, 2 eq.) at 0° C. The solution containing the β-ketophosphonate was finally added to the borohydride solution at 0° C. The resulting mixture was allowed to warm to room temperature slowly and stirred for an additional 15 hours. At this time the reaction was quenched with a saturated solution of ammonium chloride. The resulting solution was extracted with 4 equivalents of 15 mLs of ethyl acetate. The organic layers were combined, washed once with brine and dried with magnesium sulfate and evaporated to dryness. The crude material was finally purified through flash chromatography. $^1$H NMR (300 MHz, $CDCl_3$) δ 8.21 (s, 1H), 7.12 (d, J=8.5, 2H), 6.91 (d, J=8.6, 2H), 5.91 (d, J=9.3, 1H), 5.09 (s, 2H), 4.08-3.93 (m, 2H), 3.75 (s, 3H), 3.68 (dd, J=5.3, 11.0, 6H), 3.44 (s, 1H), 2.82 (d, J=7.9, 2H), 2.29 (s, 3H), 2.23 (s, 3H), 2.13 (t, J=7.3, 2H), 1.92 (m, 3H), 1.56 (s, 2H), 1.22 (s, 28H), 0.85 (t, J=6.7, 3H). $^{13}$C NMR (75 MHz, $CDCl_3$) δ 173.69, 164.53, 157.66, 154.45, 149.23, 130.44, 130.04, 126.73, 115.11, 115.04, 71.01, 68.64, 66.02, 60.09, 55.40, 52.84, 37.48, 37.06, 34.42, 32.13, 29.91, 29.57, 29.42, 25.87, 22.90, 14.34, 13.58, 11.15.

(S)-2-hydroxy-4-(4-((4-methoxy-3,5-dimethylpyridin-2-yl)methoxy)phenyl)-3-palmitamidobutylphosphonic acid, (f17)

To a dry round bottom flask containing the β-hydroxyphosphonate (0.114 g, 1 eq.) was added 1.7 mLs of dichloromethane; the mixture was cooled to 0° C. Next bromotrimethylsilane (0.260 g, 10 equivalents) was added and the reaction mixture was allowed to warm to room temperature. Once the reaction appeared to be completed by TLC analysis, 1.7 mLs of a solution of 5% water in methanol was added and the reaction mixture was stirred for an additional 15 hours. After this time the reaction mixture was evaporated to dryness and the title product was recovered as an off-white solid by recrystallization with methanol, diethyl ether and hexanes. $^1$H NMR (500 MHz, CD3OD) δ 8.49 (s, 1H), 7.26 (dd, J=8.7, 11.2, 2H), 7.09 (dd, J=6.0, 8.6, 2H), 5.40 (d, J=3.8, 2H), 4.14-4.09 (m, OH), 4.09-4.02 (m, OH), 3.96 (d, J=9.4, OH), 3.12 (dd, J=3.6, 14.2, OH), 2.93 (dd, J=5.5, 13.9, OH), 2.78 (dd, J=9.6, 13.8, OH), 2.60 (dd, J=11.0, 14.1, OH), 2.50 (s, 1H), 2.39 (s, 1H), 2.25-2.02 (m, 1H), 1.93 (ddd, J=7.1, 11.2, 12.7, OH), 1.56-1.45 (m, OH), 1.43-1.37 (m, OH), 1.27 (dd, J=14.9, 31.2, 7H), 0.89 (t, J=7.0, 1H). $^{13}$C NMR (126 MHz, DMSO) δ 173.02, 171.08, 169.21, 156.08, 143.16, 133.33, 130.62, 128.66, 127.85, 69.43, 65.84, 61.61, 40.45, 40.29, 40.12, 39.95, 39.79, 39.62, 39.45, 35.77, 34.43, 31.75, 29.52, 29.01, 25.74, 22.55, 14.20, 10.99.

EXAMPLE 2

Choline Detection Assay for ATX

The phosphonate derivatives were tested in choline detection assay for ATX inhibition. The ATX activity assay was conducted in 0.1 ml, buffer: (in mM: Tris-HCl 100, pH9, NaCl 150, MgCl$_2$ 5, CoSO$_4$ 0.03, 0.05% Triton X-100), 1 mM 18:1 LPC, using recombinant human ATX with or without test compounds; incubation was for 16 hours at 37° C. The released choline was detected as follows: Samples were mixed with 0.15 ml of 50 mM TrisHCl containing 2.7 mM TOOS(N-ethyl-N-2-hydroxy-3-sulfopropyl)-m-toluidine, 2.7 mM 4-AAP (4-aminoantipyrine), 47.7 U/ml horseradish peroxidase, 18 U/ml choline oxidase, and 5 mM MgCl$_2$. After 30 min incubation at 37° C., light absorbance (550 nm) was determined, and the amount of choline release was calculated from a standard curve.

The ATX activity was measured in the presence of the test compounds under different concentrations (100 μM, 10 μM and 1 μM). The ATX activity without TEST compounds was used as the standard (100% activity). Some β-hydroxy phosphonate derivatives inhibited ATX activity at only the highest concentration tested. Compounds f17 and f18 exhibited significant inhibition at 1 μM (Table 1). These two compounds were synthesized from protected L-tyrosine and they are diastereomers. The less polar isomer, f17, (also known as VPC8a202) was able to inhibit 73% of ATX activity at 1 μM. Compounds f15 and f16, which were synthesized from D-tyrosine, did potently inhibit ATX although they contained the same 4-methoxy-3,5-dimethyl-pyridyl structure moiety.

Further structure optimization was made based on the two lead compounds f17 and f18. A series of β-hydroxy phosphonate derivatives with a variety of lipophilic tails was prepared and tested. These data are presented in Table 2. The corresponding β-keto phosphonate derivatives were also tested (Table 3). At the concentration of 100 μM, some compounds inhibited 50%-70% of ATX activity.

TABLE 1

ATX inhibitory evaluation of compound f1-f34

IIA

| Compounds | R | * S/R | ATX activity (%) | | |
|---|---|---|---|---|---|
| | | | 1 μM | 10 Mm | 100 μM |
| f1 | pyridyl-CH$_2$-O-CH$_2$CF$_3$ | R (a$^1$) | 92 | 84 | 55 |
| f2 | pyridyl-CH$_2$-O-CH$_2$CF$_3$ | R (b$^1$) | N/D | 84 | 64 |
| f3 | pyridyl-CH$_2$-O-CH$_2$CF$_3$ | S (a) | 92 | 80 | 32 |
| f4 | pyridyl-CH$_2$-O-CH$_2$CF$_3$ | S (b) | 103 | 83 | 56 |
| f5 | benzyl | R (a) | 83 | 82 | 83 |
| f6 | benzyl | R (b) | 80 | 81 | 83 |

TABLE 1-continued
ATX inhibitory evaluation of compound f1-f34
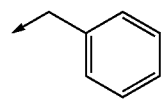
IIA
| Compounds | R | * S/R | ATX activity (%) | | |
|---|---|---|---|---|---|
| | | | 1 μM | 10 Mm | 100 μM |
| f7 | 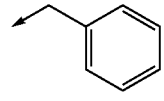 | S (a) | 97 | 77 | 68 |
| f8 | 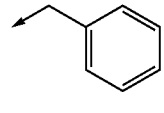 | S (b) | 76 | 83 | 78 |
| f9 | 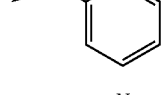 | R (a) | 103 | 76 | 60 |
| f10 | 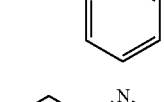 | R (b) | 92 | 78 | 69 |
| f11 | 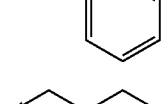 | S (a) | 104 | 81 | 52 |
| f12 | 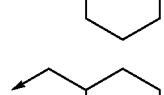 | S (b) | N/D | 74 | 65 |
| f13 | 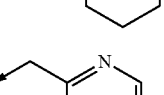 | R (b) | 84 | 80 | 67 |
| f14 | 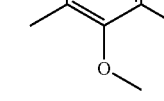 | S (b) | 80 | 80 | 80 |
| f15 | 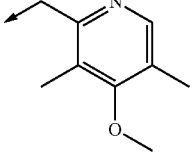 | R (a) | 108 | 95 | 63 |
| f16 |  | R (b) | 69 | 64 | 47 |

TABLE 1-continued

ATX inhibitory evaluation of compound f1-f34

IIA

[Structure of compound IIA: phosphonate group (HO)$_2$P(O)-CH$_2$-CH(OH)-CH(NHC(O)-C$_{15}$H$_{31}$)-CH$_2$-C$_6$H$_4$-OR$^1$]

| Compounds | R | * S/R | ATX activity (%) 1 μM | 10 Mm | 100 μM |
|---|---|---|---|---|---|
| f17 | 2,5-dimethyl-4-methoxypyridin-3-ylmethyl | S (a) | 27 | 13 | 6 |
| f18 | 2,5-dimethyl-4-methoxypyridin-3-ylmethyl | S (b) | 63 | 21 | 8 |
| f19 | CH$_3$ | R (a) | 100 | 78 | 57 |
| f20 | CH$_3$ | R (b) | 95 | 84 | 82 |
| f21 | CH$_3$ | S (a) | 77 | 56 | 36 |
| f22 | CH$_3$ | S (b) | 84 | 80 | 69 |
| f23 | n-C$_3$H$_7$ | R (a) | 80 | 79 | 72 |
| f24 | n-C$_3$H$_7$ | R (b) | 108 | 108 | 90 |
| f25 | n-C$_3$H$_7$ | S (a) | 110 | 97 | 77 |
| f26 | n-C$_3$H$_7$ | S (b) | 100 | 100 | 83 |
| f27 | n-C$_5$H$_{11}$ | R (a) | 81 | 85 | 80 |
| f28 | n-C$_5$H$_{11}$ | R (b) | 86 | 82 | 70 |
| f29 | n-C$_5$H$_{11}$ | S (a) | 98 | 83 | 67 |
| f30 | n-C$_5$H$_{11}$ | S (b) | 94 | 90 | 70 |
| f31 | isohexyl | R (a) | 103 | 104 | 72 |
| f32 | isohexyl | R (b) | N/D | 104 | 94 |
| f33 | isohexyl | S (a) | 104 | 104 | 82 |
| f34 | isohexyl | S (b) | 106 | 101 | 91 |

* a refers to the diastereomer that elutes first, b refers to the diastereomer that elutes second.

TABLE 2

ATX inhibitory evaluation of compound f35-f44

Structure IIB: phosphonic acid derivative with 4-methoxy-3,5-dimethylpyridin-2-yl)methoxy]phenyl core linked to amide with $R^2$.

| Compounds | R | *S/R | ATX activity (%) 1 μM | ATX activity (%) 10 μM | ATX activity (%) 100 μM |
|---|---|---|---|---|---|
| f35 | n-$C_9H_{19}$ | R (a[1]) | N/D | 86 | 30 |
| f36 | n-$C_9H_{19}$ | R (b[1]) | N/D | N/D | N/D |
| f37 | n-$C_{13}H_{27}$ | R (a) | N/D | 99 | 67 |
| f38 | n-$C_{13}H_{27}$ | R (b) | N/D | N/D | 35 |
| f39 | n-$C_{17}H_{35}$ | S (a) | 101 | 91 | 81 |
| f40 | n-$C_{17}H_{35}$ | S (b) | N/D | 90 | 62 |
| f41 | n-$C_{17}H_{33}$[2] | S (a) | N/D | 45 | 15 |
| f42 | n-$C_{17}H_{33}$[2] | S (b) | 77 | 68 | 58 |
| f43 | n-$C_{19}H_{39}$ | S (a) | 64 | 45 | 10 |
| f44 | n-$C_{19}H_{39}$ | S (b) | N/D | N/D | N/D |

[1] a refers to the diastereomer that elutes first, b refers to the diastereomer that elutes second.
[2] cis double bond located between C9 and C10 from the carbonyl.

TABLE 2

ATX inhibitory evaluation of compound g1-g15

Structure with phosphonic acid, hydroxyl, amide-linked pentadecyl chain, and 4-($R^1$O)phenyl core.

| Compounds | R | *S/R | ATX activity (%) 1 μM | ATX activity (%) 10 μM | ATX activity (%) 100 μM |
|---|---|---|---|---|---|
| g1 | 2-methylene-4-(2,2,2-trifluoroethoxy)pyridine | R | 85 | 70 | 57 |
| g2 | 2-methylene-4-(2,2,2-trifluoroethoxy)pyridine | S | 79 | 68 | 44 |
| g3 | benzyl | R | N/D | 82 | 76 |
| g4 | benzyl | S | N/D | 71 | 61 |
| g5 | pyridin-2-ylmethyl | R | 78 | 68 | 52 |

TABLE 2-continued

ATX inhibitory evaluation of compound g1-g15

[Chemical structure: a phosphonate compound with HO-P(=O)(OH)-CH2-CH(OH)-CH(NHC(=O)-long alkyl chain)-CH2-phenyl-O-R1]

| Compounds | R | *S/R | ATX activity (%) 1 µM | 10 µM | 100 µM |
|---|---|---|---|---|---|
| g6 | [2-pyridylmethyl] | S | 102 | 72 | 50 |
| g7 | [4-methoxy-3,5-dimethyl-2-pyridylmethyl] | S | 71 | 74 | 26 |
| g8 | CH₃ | R | 84 | 71 | 32 |
| g9 | CH₃ | S | 96 | 68 | 45 |
| g10 | n-C₃H₇ | R | 104 | 97 | 75 |
| g11 | n-C₃H₇ | S | N/D | 97 | 72 |
| g12 | n-C₅H₁₁ | R | 93 | 84 | N/D |
| g13 | n-C₅H₁₁ | S | 95 | 83 | N/D |
| g14 | isopentyl | R | 97 | 101 | 76 |
| g15 | isopentyl | S | 104 | 104 | 85 |

EXAMPLE 3

Kinetic Study of f17 Inhibition of ATX

Human recombinant autotaxin (ATX) was subcloned into the mammalian expression vector pcDNA3.1/V5His-TOPO (Invitrogen) and expressed as a C-terminus V5- and 6×His-tagged protein in HEK-293 cells using PolyFect® (Qiagen) as a transfection reagent. ATX was purified from the culture medium using a nickel-Sepharose resin (Qiagen) according to manufacturer's instructions and the buffer was changed to PBS using 30 kDa cutoff Centricon tubes (Millipore). ATX DNA was generated from an EST I.M.A.G.E. clone 5174518 using forward and reverse primers, to amplify the ATX coding sequence. ATX activity was measured essentially as described by Umezu-Goto M., et al., J Cell Biol, 158: 227-233, 2002, by determining the release of choline after incubation at 37° C. for 18 h in 0.1 ml of a buffer consisting of 100 mM Tris-HCl, pH 9.0, 500 mM NaCl, 5 mM MgCl$_2$, 0.03 mM CoCl$_2$, 0.05% Triton X-100, 0.5 µM of f17 and various concentrations of oleoyl-LPC (lysophosphatidylcholine, Avanti Polar Lipids, Alabaster, Ala.). Choline was detected colorimetrically as absorbance of light (555 nm) after adding 0.1 ml of 50 mM Tris-HCl, pH 8.0, 5 mM MgCl$_2$, 50 U/ml horseradish peroxidase, 18 U/ml choline oxidase, 5 mM 4-aminoantipyrine, and 3 mM N-ethyl-N-(2-hydroxy-3-sulfopropyl)-m-toluidine.

Results

Using non-linear regression on the direct plot values were (values are averages of three measurements):

−VPC8a202: Vmax=1.54, Km=0.87 mM

+VPC8a202: Vmax=1.41, Km=1.19 mM Ki for VPC8a202=1.3 µM

Figure 2:
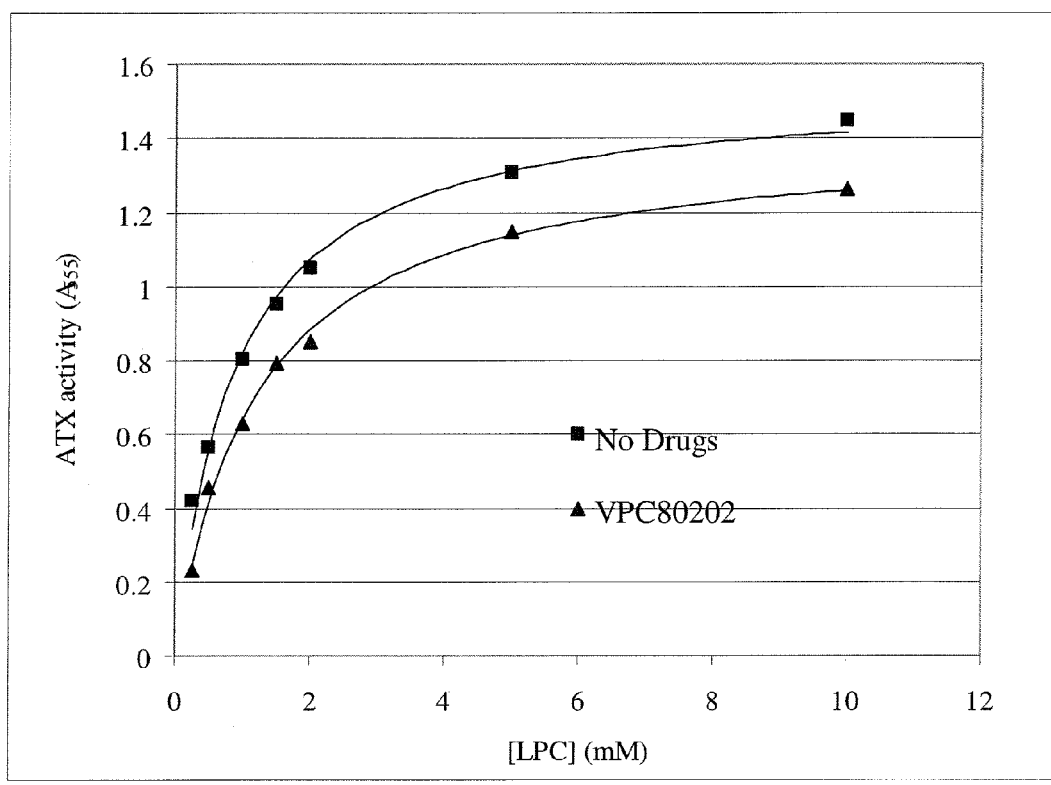
FIG. 2 and FIG. 3 illustrate the kinetics of inhibition of ATX activity with test compound f17 (VPC8a202). The initial rate of recombinant ATX activity was measured calorimetrically at different concentrations of LPC in presence and absence of 0.5 µM VPC8a202. Activity was expressed as the release of choline during 18 hours and it is represented by the absorbance of the product at 555 nm (A555). Each point is the average of three measurements (FIG. 2). Consumed substrate was less than 10% in every case thus ensuring an initial rate of reaction.

The results are illustrated in FIG. 2.

Using linear regression on the double reciprocal plot values were:

−VPC 8a202: Vmax=1.35, Km=0.59 mM

+VPC 8a202: Vmax=1.50, Km=1.34 mM Ki for VPC8a202=0.39 µM

Figure 3:
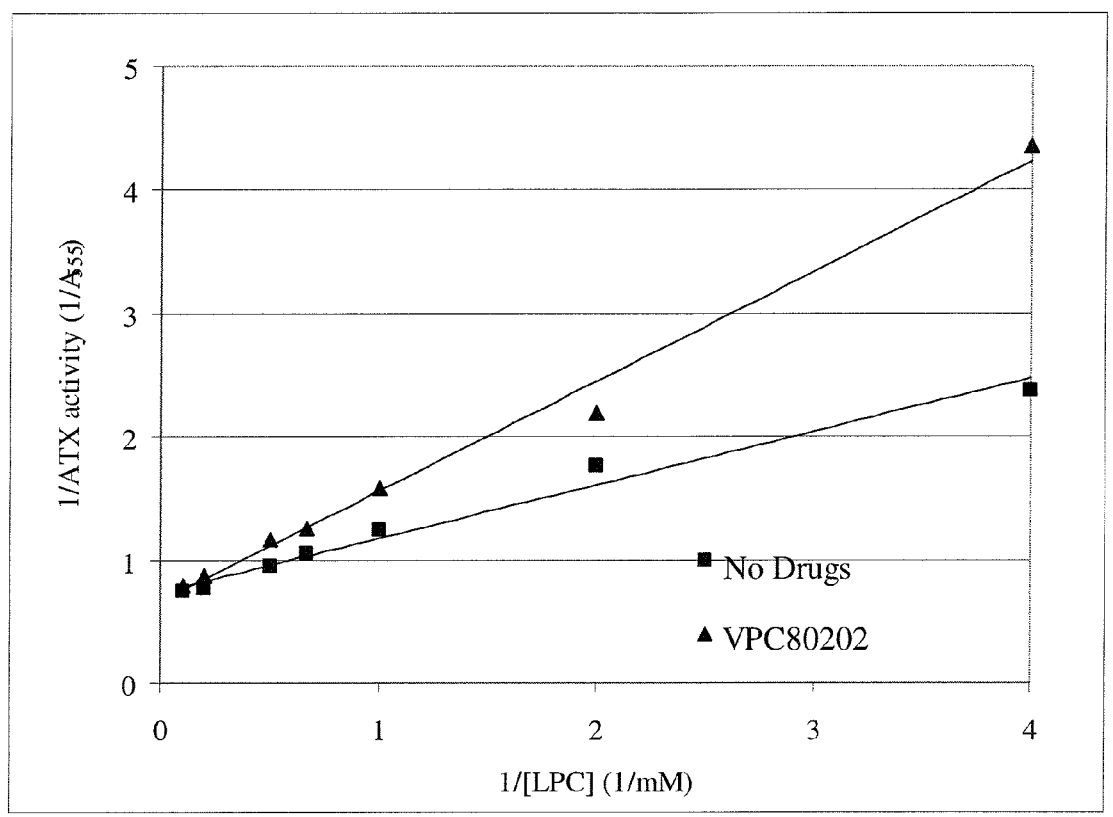

The results are illustrated in FIG. 3.

The disclosures of each and every patent, patent application, and publication cited herein are expressly incorporated herein by reference in their entirety into this disclosure. illustrative embodiments of this disclosure are discussed and reference has been made to possible variations within the scope of this disclosure. These and other variations and modifications in the disclosure will be apparent to those skilled in the art without departing from the scope of the disclosure, and it should be understood that this disclosure and the claims shown below are not limited to the illustrative embodiments set forth herein.

The invention claimed is:
1. A compound of the formula:

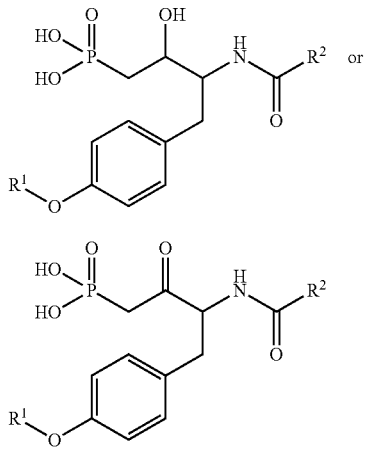

wherein
R$^1$ is C$_1$-C$_6$ alkyl, or methyl substituted with cyclohexyl, phenyl, or pyridyl; where the cyclohexyl, phenyl, or pyridyl are optionally substituted with methyl, methoxy, 2,2,2-trifluoroethoxy or combinations thereof;
R$^2$ is C$_9$-C$_{19}$ alkyl;
or a pharmaceutically acceptable salt or ester thereof.
2. The compound of claim 1, wherein R$^1$ is CH$_3$, n-C$_3$H$_7$, n-C$_5$H$_{11}$, i-C$_5$H$_{11}$,

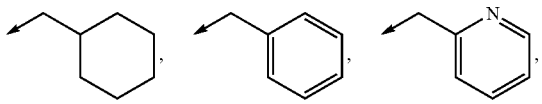

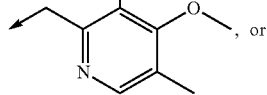

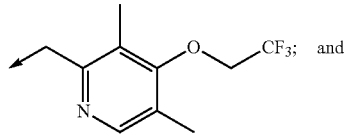

R$_2$ is n-C$_9$H$_{19}$, n-C$_{13}$H$_{27}$, n-C$_{15}$H$_{31}$, n-C$_{17}$H$_{33}$, n-C$_{17}$H$_{35}$, or n-C$_{19}$H$_{39}$.

3. The compound of claim 2, wherein R$^1$

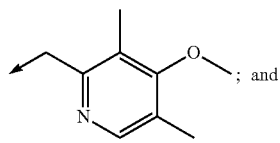

R$_2$ is n-C$_{13}$H$_{27}$, n-C$_{15}$H$_{31}$, or C$_{17}$H$_{35}$.

4. The compound of claim 3, of the formula:

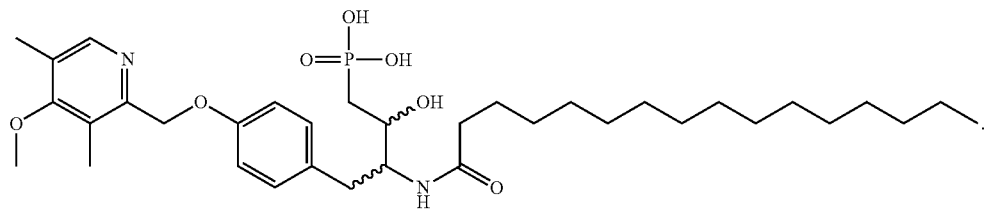 [SMILES: CCCCCCCCCCCCCCCC(=O)NC(Cc1ccc(OCc2ncc(C)c(OC)c2C)cc1)C(O)CP(=O)(O)O]

5. The compound of claim 4, of the formula:

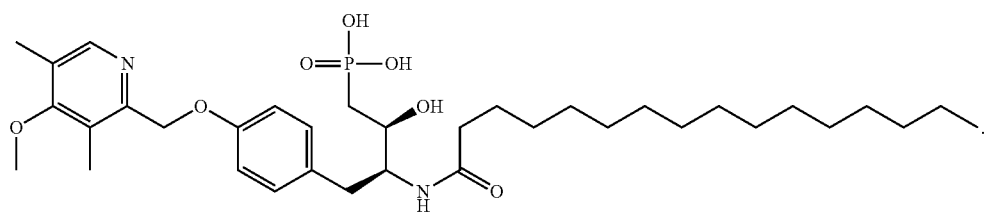 [SMILES: CCCCCCCCCCCCCCCC(=O)N[C@@H](Cc1ccc(OCc2ncc(C)c(OC)c2C)cc1)[C@H](O)CP(=O)(O)O]

6. The compound of claim 4, of the formula:

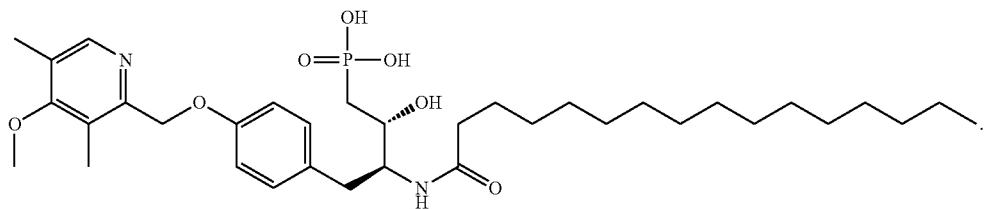 [SMILES: CCCCCCCCCCCCCCCC(=O)N[C@@H](Cc1ccc(OCc2ncc(C)c(OC)c2C)cc1)[C@@H](O)CP(=O)(O)O]

7. The compound of claim 4, of the formula:

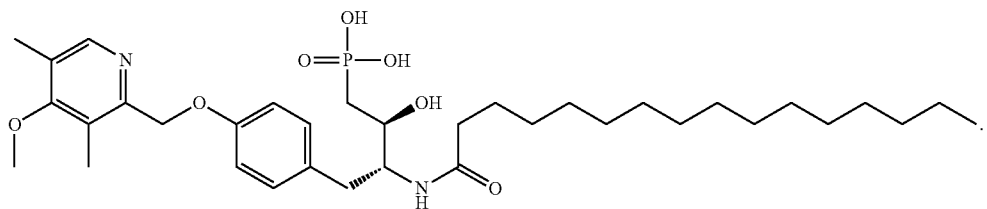 [SMILES: CCCCCCCCCCCCCCCC(=O)N[C@H](Cc1ccc(OCc2ncc(C)c(OC)c2C)cc1)[C@H](O)CP(=O)(O)O]

8. The compound of claim 4, of the formula:

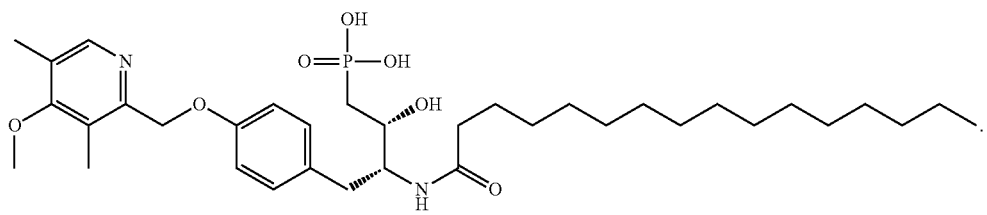 [SMILES: CCCCCCCCCCCCCCCC(=O)N[C@H](Cc1ccc(OCc2ncc(C)c(OC)c2C)cc1)[C@@H](O)CP(=O)(O)O]

9. A composition comprising a compound of claim 1 and a pharmaceutically acceptable carrier.

10. The composition of claim 9, wherein the pharmaceutically acceptable carrier is a liquid.

11. The composition of claim 9, which is an oral dosage form.

12. The composition of claim 9, which is adapted for parenteral, aerosol or transdermal administration.

* * * * *